United States Patent [19]

Mayer

[11] Patent Number: 4,536,670

[45] Date of Patent: Aug. 20, 1985

[54] ELECTRICAL BRUSHES WITH WEAR SENSORS

[75] Inventor: Leonard C. Mayer, Dunn, N.C.

[73] Assignee: Morganite Incorporated, Dunn, N.C.

[21] Appl. No.: 330,723

[22] Filed: Dec. 14, 1981

[51] Int. Cl.³ .............................................. H02K 13/00
[52] U.S. Cl. ...................................... 310/249; 310/245
[58] Field of Search .............................. 310/248–253, 310/242, 245, 247, 238, 42; 200/61.4, 308, 61.41; 340/648, 671

[56] References Cited

U.S. PATENT DOCUMENTS

| | | | |
|---|---|---|---|
| 1,253,265 | 1/1918 | McKeown | 310/248 |
| 1,485,942 | 3/1924 | Adams | 310/249 |
| 2,098,062 | 11/1937 | Palmer | 310/249 |
| 3,153,164 | 10/1964 | Jop | 310/249 |
| 3,681,635 | 8/1972 | Bayer | 310/248 |
| 4,316,186 | 2/1982 | Purdy | 310/245 |
| 4,333,095 | 6/1982 | Silva | 310/245 |

FOREIGN PATENT DOCUMENTS

| | | | |
|---|---|---|---|
| 0023537 | 2/1981 | European Pat. Off. | 310/249 |
| 2804547 | 8/1979 | Fed. Rep. of Germany | 310/249 |
| 795998 | 6/1958 | United Kingdom | 310/248 |
| 1158298 | 7/1969 | United Kingdom | 310/245 |
| 1262486 | 2/1972 | United Kingdom | 310/249 |

Primary Examiner—R. Skudy
Attorney, Agent, or Firm—William R. Hinds

[57] ABSTRACT

An electrical brush has a brush wear sensor incorporated in the brush body to indicate when the brush has worn to a predetermined point. The sensor comprises a length of insulated electrical wire doubled back onto itself intermediate its ends and located in a passageway, preferably a blind bore, extending from a surface remote from the wear surface at least to the point at which brush wear is to be sensed. The end of the doubled back portion extends to the point at which wear is to be sensed, and the ends extend from the brush body for connection to one or more electrical sensors. A cement in the passageway retains the doubled wire, and the wires of the doubled wire may be twisted or looped about each other to increase adherence and retention. When the brush wears to the tip of the doubled wire, the wire insulation wears away, and contact of the conducting wire or wires with the commutator or the like is sensed. The use of a doubled twisted wire ensures against inadvertent pullout, avoids erroneous signals which could arise from the specially insulated end of a single cut wire, and provides for separate signals or a backup signal to the same sensor.

7 Claims, 4 Drawing Figures

ELECTRICAL BRUSHES WITH WEAR SENSORS

FIELD OF THE INVENTION

This invention relates to electrical brushes of the type having a wear sensor in the form of an electrical conductor or lead within the brush body, normally insulated, but adapted to emit a detectable signal when the insulation is worn away upon wear of the brush to a predetermined point.

BACKGROUND AND SUMMARY

As is well known, electrical brushes are merely devices for conducting current to or from a rotating part. Typically, the brush is stationary, and is held and guided by a fixed brush holder in which it slides freely. There may be several brushes side by side to form a single brush set. The rotating member may be the commutator of a direct current machine or the slip rings or the like of an alternating current machine, but in general brushes are usable in any instance where current is to be passed from one member to a relatively movable member. A typical brush material is carbon, to which circuit connections are made by means of short flexible cables. Brushes wear and must be replaced periodically, and it is known in the art to provide brush wear sensors, typically in the form of an electrical wire or the like incorporated in but insulated from the brush body, and so located as to activate a sensor or signal when the insulation is worn away when brush wear reaches a predetermined point.

A typical previous approach has been to use a length of standard Teflon (trademark) coated wire, cut square at one end and sealed with an insulating cement to insulate the exposed wire tip. This wire is then cemented into a blind hole, typically slightly deeper than, and parallel to, the main conductors extending into the brush body. When the brush wears to the wire tip, and the wire tip sealant wears away, the circuit to a signal is completed. Difficulties have been encountered in anchoring such single wires because of the nature of the required high temperature insulating material, typically being polymers of fluoroethylene, having a smooth, generally inert surface that is difficult to bond in the brush body. Additionally, there has been the problem of insulating the cut end of the wire to insulate this cut end from the brush. Silicone sealants have been tried and have been successful to some extent, but silicone can be detrimental to brush performance. Additionally, there is the possibility of faulty application of the insulating sealant, which will result in a false signal. Additionally, creep of the original insulation adjacent its cut end can result in exposure of the conducting wire to the brush material.

In general, the concept of the instant invention utilizes the normal wire insulation itself to insulate the wire from the brush body, such that there are no insulation discontinuities within the brush body, and there is no need to apply a special insulator material to any part of the wire in the brush body. Basically, the invention utilizes an insulated wire doubled back onto itself intermediate its ends and located in a passageway such as a blind bore in the brush body such that the doubled back portion extends to the point at which brush wear is to be sensed and the ends extend from the brush body for connection to one or more electrical signal or sensor devices. Thus, the normal wire insulation is continuous within the brush body. The doubled wire length within the brush body is secured in position by a suitable cement. To minimize the possibility of inadvertent pull-out, it is preferred to twist the individual wire segments of the doubled wire about each other, since after the cement adheres to the brush material and sets, the wire is additionally mechanically held. This precludes failure due to nonadherence of the cement to the insulation on the wire.

It might be expected that brushes would be replaced promptly after the wear indicator signal is activated, such that a continuous signal thereafter would not be necessary. However, it must be assumed that brushes will not be replaced immediately, and cases can be expected where replacement does not occur for some time. Therefore, it is preferred that the sensor wire be cemented over substantially the full depth of the blind pole, such that the wires would remain in the hole and continue to provide a wear signal until the brush is actually replaced.

In those wear sensors utilizing a single wire, there is the possibility that the insulation might pull across the wire end while being worn away, in which case there would not be a signal since there would be no contact at times. This is also true of the doubled wire approach to some extent, but the double wire in essence provides to opportunities at making contact. As such, the double wire can have both ends connected to one terminal, or the two ends could lead to different functional applications, such as having one end lead to a wear indicator light and the second end lead to a lift-off timer circuit.

Other features and advantages of the invention will become apparent to those skilled in the art from the ensuing description of preferred embodiments, taken in conjunction with the appended drawings.

DESCRIPTION OF THE PREFERRED EMBODIMENTS

Figure 1:
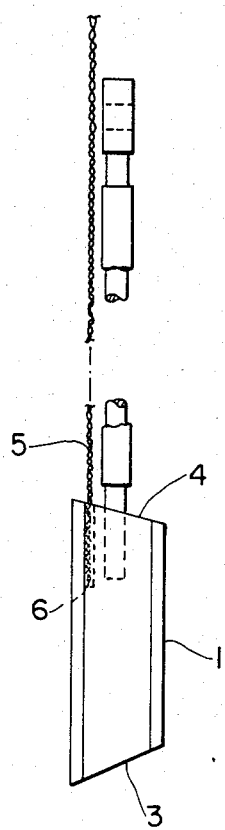
FIG. 1 is an elevational view of a typical carbon brush incorporating a brush wear sensor in accordance with the invention.
Figure 2:
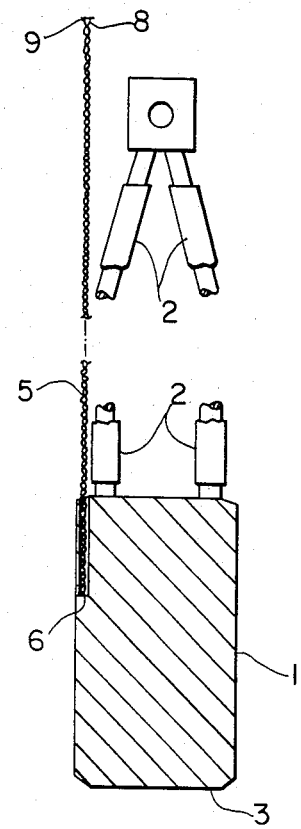
FIG. 2 is a frontal view corresponding to FIG. 1, but partially in section.
Figure 3:
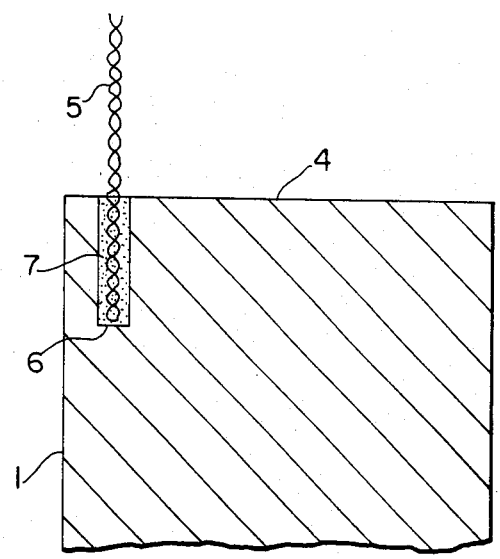
FIG. 3 is an enlarged fragmentary view corresponding to FIG. 2, but showing more detail.
Figure 4:
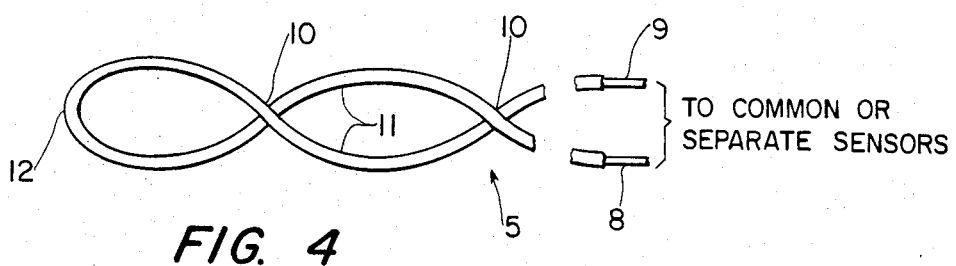
FIG. 4 is a diagrammatic illustration of the doubled-back wire twisted or looped about each other in a preferred manner.

As shown, a carbon brush body 1 has a commutator contacting, wear surface 3 and an upper or outer surface 4. Silastomer sleeved flexible conductors 2 of conventional type lead from and are connected to the brush body, being located therein by, for example, tamped copper powder connections. The brush itself and its main conductors are entirely conventional. A blind bore 6 extends from the upper surface of the brush body to the point at which brush wear is to be sensed, typically slightly below the lower ends of the main conductors to ensure sensing of brush wear prior to exposure of the main conductor ends. Typically this clearance might be of the order of 0.062 inches. A brush wear sensor 5 comprises a length of wire insulated with Teflon (trademark) doubled back on itself intermediate its ends 8 and 9 to form a looped portion such that the end 12 of the doubled wire extends to the bottom of the blind bore 6. The entire length of doubled wire within the blind bore is secured therein by filling the bore with a cement 7. To enhance retention, the double wire preferably is twisted as illustrated diagrammatically in FIG. 4 such that the wires are twisted about each other at spaced points 10 which separate adjacent looping portions 11 from each other. The stripped free ends can be connected to a common terminal so as to provide a double signal path, or they can be separately connected to individual sensors or other devices (not shown in the drawing).

From the foregoing, it will be readily apparent that when the brush wears to the bottom of the blind bore 6, the insulation at tip 12 of the wire sensor will begin to wear away, resulting in contact of the conducting wire with the commutator, and the generation of a signal or signals at terminal ends 8 and 9. Even if the brush is not replaced promptly thereafter, the signal will continue, and, since the sensor wires are firmly embedded in the brush body by the cement, the wires will not become loose so as to contact other moving electrically live surfaces.

An exemplary wire material is No. 30 AWG Teflon-coated wire, the Teflon insulation preferably being etched, although standard unetched insulation is entirely workable. Any suitable cement, such as epoxy resin, can be used to anchor the wire sensor in the blind bore. As between etched and unetched wire insulation, the etched is preferred in that it provides a higher pull-out resistance, and wire with etched Teflon insulation is much easier to handle. In pull tests using unetched wire, the results were 6 pounds average, 2.5 pounds minimum and 10 pounds maximum, relative to a probably acceptable level of 2 pounds pull resistance. Using etched wire, the corresponding results were 16 pounds average, 12 pounds minimum and 22 pounds maximum. In the twisted embodiment, an average of 6 twists per inch has been found to be entirely satisfactory.

The invention, of course, is not limited to the particular materials and structural features disclosed and described herein, since various alternatives will be readily apparent. For instance, while the provision of a blind bore leading from the outer surface of the brush body is much preferred, there conceivably could be provided a slot or groove in one of the side surfaces of the brush body, into which the doubled wire sensor could be cemented. Accordingly, it should be understood that the scope of the invention is as defined in the appended claims, interpreted in the light of the foregoing specification and drawings.

Having thus described the invention as required, including exemplary preferred embodiments thereof, I claim:

1. An electrical brush comprising a brush wear sensor, including a brush body having a wear surface, a passageway in said brush body extending from a surface remote from said wear surface at least to the point at which brush wear is to be sensed, a length of insulated electrical conductor doubled back onto itself intermediate its ends to form a looped portion and located in said passageway such that the doubled back looped portion extends to said point at which brush wear is to be sensed and said ends extend from the brush body for connection of at least one of the ends to an electrical sensor means, at least part of said doubled back insulated conductor in said passageway being twisted such that each insulated conductor is twisted about the other, and a cement retaining said doubled and twisted insulated electrical conductor in said passageway.

2. A device as claimed in claim 1 wherein said passageway is a hole in said brush body.

3. A device as claimed in claim 2 wherein said passageway is a blind hole leading from said point to a body surface remote from said wear surface.

4. A device as claimed in claim 3 wherein said electrical conductor is insulated wire.

5. A device as claimed in claim 4 wherein each wire is twisted about the other at spaced points separating adjacent looping portions from each other along the length of the doubled back wire.

6. A device as claimed in claim 5 wherein said cement fills substantially the entire length of said blind hole and thus secures substantially the entire length of wire therein.

7. A device as claimed in claim 4 wherein the wire ends are free of each other so as to be separately connectable to different electrical sensors.

* * * * *